United States Patent
Xiao et al.

(10) Patent No.: US 10,927,137 B2
(45) Date of Patent: Feb. 23, 2021

(54) METHOD FOR PREPARING OLIGOMERIC MANNURONIC DIACID

(71) Applicant: Shanghai Green Valley Pharmaceutical Co., LTD., Shanghai (CN)

(72) Inventors: Zhongping Xiao, Shanghai (CN); Zhenqing Zhang, Suzhou (CN); Meiyu Geng, Shanghai (CN); Jian Ding, Shanghai (CN)

(73) Assignee: Shanghai Green Valley Pharmaceutical Co., LTD., Shanghai (CN)

( * ) Notice: Subject to any disclaimer, the term of this patent is extended or adjusted under 35 U.S.C. 154(b) by 82 days.

(21) Appl. No.: 16/325,961

(22) PCT Filed: Aug. 15, 2016

(86) PCT No.: PCT/CN2016/095368
§ 371 (c)(1),
(2) Date: Feb. 15, 2019

(87) PCT Pub. No.: WO2018/032272
PCT Pub. Date: Feb. 22, 2018

(65) Prior Publication Data
US 2020/0055888 A1    Feb. 20, 2020

(51) Int. Cl.
*C07H 7/033*    (2006.01)
*C07H 1/00*    (2006.01)

(52) U.S. Cl.
CPC .............. *C07H 7/033* (2013.01); *C07H 1/00* (2013.01)

(58) Field of Classification Search
CPC ......... C08B 37/0084; C07H 1/00; C07H 7/033
USPC ....................................... 536/123.1
See application file for complete search history.

(56) References Cited

FOREIGN PATENT DOCUMENTS

| EP | 1736160 A1 | * 12/2006 | ............. C08B 37/00 |
| GB | 289280 | * 4/1928 | |
| JP | 2007230902 A | 9/2007 | |
| JP | 2007530718 A | 11/2007 | |
| WO | 02/32913 A1 | 4/2002 | |

OTHER PUBLICATIONS

Thaburet et al, Carbohydrate Research, 2001, 330, 21-29.*
Varela, Oscar, Advances in Carbohydrate Chemistry and Biochemistry, 2003, 58, 307-369.*
Grgur, Branimir N. et al., "A kinetic study of D-glucose oxidation by bromine in aqueous solutions." Carbohydrate Research 341 (2006) 1779-1787.
Extended European Search Report for 16913036.6 (based on PCT/CN2016/095368) dated Mar. 11, 2020.
Varela, Oscar. "Oxidative Reactions and Degradations of Sugars and Polysaccharides." Advances in Carbohydrate Chemistry and Biochemistry, vol. 58. p. 307-369, 2003.

* cited by examiner

*Primary Examiner* — Ganapathy Krishnan
(74) *Attorney, Agent, or Firm* — Womble Bond Dickinson (US) LLP; Cristin Cowles; Sai Seetharaman (57) ABSTRACT

The invention relates to a new method of preparing oligomannuronic diacids, important bioactives. The method utilizes oligomannuronic acids as starting materials and the target substances are obtained by acid degradation and active hypobromous acid oxidation steps. The method of preparing oligomannuronic diacids according to the invention employs moderate reaction conditions, has few side reactions, does not need further purification, achieves a yield of more than 90%, or even more than 95%, and is suitable for production with an on-line continuous reactor device, with reaction processes easy to implement automatic control.

17 Claims, 4 Drawing Sheets

METHOD FOR PREPARING OLIGOMERIC MANNURONIC DIACID

CROSS-REFERENCE TO RELATED APPLICATIONS

This application is a National Stage Application of International Application No. PCT/CN2016/095368, filed Aug. 15, 2016, entitled "Method For Preparing Oligomeric Mannuronic Diacid", the entire contents of which are incorporated herein by reference in their entirety.

TECHNICAL FIELD

The invention relates to a new method of preparing oligomannuronic diacids, important bioactives. The method utilizes M-segment intermediates as starting materials and obtains the target substances by acid degradation and active hypobromous acid oxidation steps.

BACKGROUND OF THE INVENTION

Oligomannuronic diacids are gaining extensive attention due to their potential pharmaceutical values. Oligomannuronic diacids are typically prepared by multiple steps from alginic acids as raw materials.

The polysaccharide molecules of the raw material alginic acids contain is M-segments formed from D-mannuronic acid via beta-1,4-glucosidic bond linkage, G-segments formed from L-guluronic acid via alpha-1,4-glucosidic bond linkage, and MG-segments formed by the hybridization of the two saccharides. Their structural formulas are shown below.

(M; beta-D-mannuronic acid)     (G; alpha-L-guluronic acid)

The M-segments and G-segments can be isolated from the raw material alginic acids. The typical method is described as follows: alginic acids are preliminarily degraded to produce mixed polysaccharides of polymannuronic acids and polyguluronic acids; then the mixed polysaccharides are precipitated by an acid method to remove the polyguluronic acids therein and further refined to obtain homopolymannuronic acids with a purity of more than 90% (referred to as "M-segment intermediates" hereinafter). Reference may be made to the methods disclosed for example in Chinese Patent Application No. 98806637.8 and CN02823707.2.

Chinese Patent Application 200580009396.5 and U.S. Pat. No. 8,835,403B2 to Geng Meiyu, et al., disclose that the derivatives of oligomannuronates, mannuronic diacids, have important pharmaceutical values. The reaction process for the mannuronic diacids can be illustrated by the following schema (I). That is, the aldehyde group at C1 position of the mannuronic acid at the polysaccharide reducing end of the oligomannuronic acid is oxidized to a carboxyl group.

During the above oxidation, oxidants used include alkali copper sulfate solution, i.e., Fehling's solution, as in U.S. Pat. No. 8,835,403. Specifically, under an alkali is condition, the reaction substrate oligomannuronic acids are added into copper sulfate solution to react in boiling water bath for from 15 mins to 2 hours. In such a method, $Cu^{2+}$ ion is used as an oxidant to oxidize the aldehyde group, and a brick-red cuprous oxide precipitate is produced during the reaction. This reaction is usually used to identify reducing saccharides.

The reaction of oxidizing glucose to gluconic acid is similar. These reactions can be categorized into three types. The first type refers to biological fermentation or enzymatic oxidation, including fermentation by, such as, *Aspergillus niger* described in Chinese Patent 96119169.4, microorganism fermentation to produce gluconic acid described in U.S. Pat. Nos. 5,962,286, 5,017,485, and 5,190,869, and glucose oxidase method described in, e.g., U.S. Pat. Nos. 6,942,997, 5,897,995, and 3,935,071. The second type refers to heavy metal catalyzed oxidation: palladium catalyzed oxidation to prepare gluconic acid, as described in U.S. Pat. Nos. 5,132, 452 and 4,843,173. The third type refers to chemical reagents: oxidation of glucose with hydrogen peroxide to prepare gluconic acid, as described in Chinese Patent No. 2011103384029.

However, there are some deficiencies in the above methods. For example, long production period and high cost for biological fermentation and enzymatic catalyzation; easy deactivation of heavy metal catalysts, and easy introduction of heavy metal residues; need for a high temperature of about 100° C. for copper hydroxide or hydrogen peroxide reaction, many side reactions, and low yield (<50%).

SUMMARY OF THE INVENTION

The inventors have found that by using specific oxidants, the reaction yield is greatly improved, the rate of the reaction to produce oligomannuronic diacids is fast, and side reactions are few. The reaction can be terminated by adding sufficient methanol or ethanol into the reaction product and obtain an oily precipitate. The oily substance is isolated with a separating funnel and dried. If refining is needed to is remove monosaccharides, salts, and organic acid impurities, it can be further achieved by dialysis or column chromatograph with simple operations.

The invention specifically relates to a method of preparing oligomannuronic diacids by oxidation of M-segment intermediates as raw materials. Specifically, the M-segment intermediates are degraded to form M-segment oligosaccharides (also referred to as "oligomannuronic acids" herein), which is further converted to the oligomannuronic diacids by oxidization with a bromine containing material as oxidant that can function as hypobromous acid, such as bromine water or active hypobromite.

The first aspect of the invention provides a method of preparing oligomannuronic diacids, comprising an oxidation reaction step of contacting oligomannuronic acids with a bromine containing oxidant. Particularly, the bromine containing oxidant for the invention is selected from the group consisting of bromine water, liquid bromine, hypobromous acid, hypobromite, the combination of a bromide ion source with hypochlorite, and the combination of bromine with hypochlorite. These oxidants function by bromine ion or hypobromite ion. In an embodiment of the invention, the molar amount of the bromine containing oxidant calculated as hypobromous acid and/or hypochlorite is 1.0-2.0 folds of the reaction raw material oligomannuronic acid.

Another aspect of the invention relates to use of an oxidant that functions via bromine ions or hypobromite ions (BrO$^-$) in the oxidation of reducing oligosaccharides or polysaccharides.

The method of preparing oligomannuronic diacids according to the invention may employ moderate reaction conditions, have few side reactions, does not need further purification, and may achieve a yield of more than 90%, or even more than 95%. The oxidation reaction of the invention has a fast rate and a high yield, can run at room temperature, and is suitable for production with an on-line continuous reactor device, with reaction processes easy to implement automatic control. The selected oxidants are cost effective, easy to handle, and suitable for large-scale manufacture.

DETAILED DESCRIPTION OF THE INVENTION

The term "about" as used herein refers to falling within the range of ±5% of the value modified with the term, and, in a preferred embodiment, falling within the range of ±3% of the value modified with the term, and, in a more preferred embodiment, falling within the range of ±1% of the value modified with the term.

Preparation of M-Segment Intermediates

The raw material M-segment intermediates used in the invention can be prepared by methods known in the prior art, e.g., the methods disclosed in Chinese Patent Application No. 98806637.8 and CN02823707.2. These methods can be simply described as follows: alginic acids are preliminarily degraded to produce mixed polysaccharides of polymannuronic acids and polyguluronic acids; then the mixed polysaccharides are precipitated by an acid method to remove the polyguluronic acids is therein and further refined to obtain homopolymannuronic acids with a purity of more than 90%.

Figure 1:
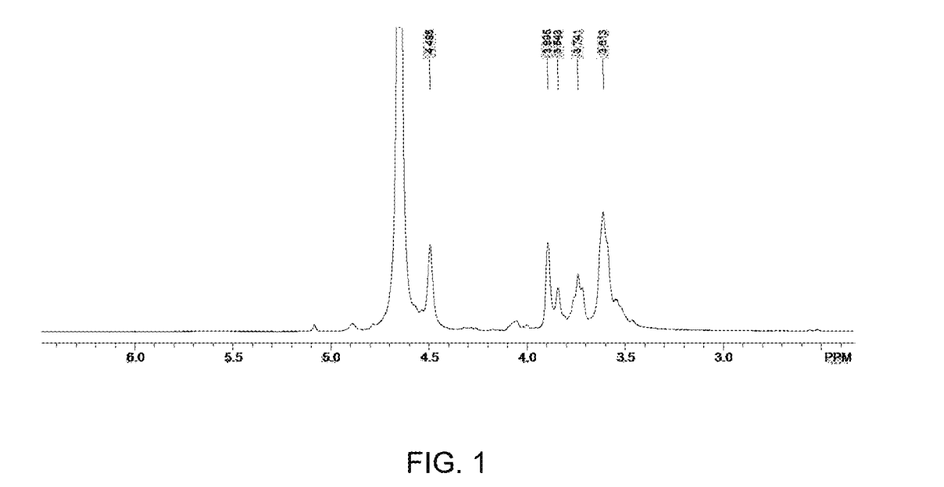
FIG. 1 shows nuclear magnetic resonance spectroscopy ($^1$H-NMR) of the raw material M-segment intermediates in the invention.

The M-segment intermediates prepared by the method have a molecular weight of around 10 KDa, and the structures are verified by H NMR spectrum ($^1$H-NMR), as shown in FIG. 1. In a specific embodiment, there is only one terminal proton signal near chemical shift value of 4.5 ppm in the H NMR spectrum, which is assigned to $^1$H at C1-position of mannuronic acid; and there are 4 hydrogen signals between 3.5 ppm 3.9 ppm, which are assigned to four $^1$H signals at C2-C5. The thus-obtained M-segment intermediates can be directly used for the next step reaction.

In a preferred embodiment, the M-segment intermediates suitable for the invention have a purity of more than 60%, preferably more than 70%, more preferably more than 80%, and a molecular weight range of 1-15 KDa, preferably 2-12 KDa, and more preferably 4-10 KDa.

Preparation of M-Segment Oligosaccharides

The M-segment intermediates are used as raw materials for acid degradation to obtain M-segment oligosaccharides to be oxidized. The M-segment intermediates are dissolved in water and formulated into a concentrated solution with a concentration of more than 15% (w/v) and then subject to acid degradation. Preferably, the formulated solution has a concentration of more than 20% (w/v), more preferably more than 25% (w/v).

Afterwards, the pH of the solution is adjusted to be acidic, preferably below 5, more preferably below 4, and most preferably below 3.5. The solution is subject to degradation at a high temperature under a high pressure and naturally cooled to room temperature.

The acid degradation is conducted under high temperature and high pressure conditions. The temperature is 95-150° C., preferably 100-130° C., and more preferably 105-120° C. The pressure is 0.10-0.50 MPa, preferably 0.10-0.28 MPa, and more preferably 0.15-0.20 MPa.

The solution after degradation is concentrated, evaporated, and dried to obtain anhydrous solids.

The M-segment oligosaccharides comprise a mixture of disaccharides to tridecasaccharides, wherein based on the weight of the mixture of disaccharides to tridecasaccharides, disaccharides to tetrasaccharides comprise about 40-60%, preferably 50%; pentasaccharides to decasaccharides comprise about 30-50%, preferably 40%; undecasaccharides to tridecasaccharides comprise about 5-15%, preferably about 10%.

Oxidation Step by Active Hypobromite

The anhydrous M-segment oligosaccharides prepared in the previous step are oxidized to prepare the oligomannuronic diacids according to the invention. The oxidant used in this step is a bromine containing oxidant. Specifically, this bromine containing oxidant is selected from the group consisting of bromine water, liquid bromine, hypobromous acid, hypobromite, the combination of a bromide ion source with hypochlorite, and the combination of bromine with hypochlorite. Since the hypobromite or hypobromite ion is not stable, the hypobromite used in the method according to the invention can be produced in situ in the reaction system, or prepared on site before it is added to the reaction solution.

In an embodiment of the invention, bromine water or liquid bromine is used as the oxidant. Bromine water as a commercially available product is available from suppliers. Generally commercially available bromine water is in a concentration of 3%.

$$RCHO+Br_2+3OH^-=RCOO^-+2Br^-+2H_2O$$

In an embodiment of the invention, hypobromite is used as the oxidant. The hypobromite may be sodium hypobromite and/or potassium hypobromite. The hypobromite is prepared in situ by adding liquid bromine and an alkali into the reaction medium. For example, it is prepared from the mixture of liquid bromine and NaOH or KOH.

By taking sodium hypobromite as an example, the chemical schemas of the is oxidation reactions thus conducted are as follows.

$$Br_2+2NaOH=NaBrO+NaBr+H_2O \quad (1)$$

$$RCHO+NaBrO=RCOOH+NaBr \quad (2)$$

In another embodiment of the invention, the hypobromite can be prepared in situ with the progress of the reaction from a metal bromide with sodium hypochlorite or potassium hypochlorite. During the reaction, the reaction solution fades, and then reddish brown color gradually appears, indicating the generation of $Br_2$. The color fades with the progress of the reaction. By taking sodium hypochlorite as an example, the chemical schemas of the oxidation reactions thus conducted are as follows.

$$RCHO + NaClO \xrightarrow{Br^-, OH^-} RCOOH + NaCl$$

Reaction Mechanism

Alternatively, in another embodiment, the hypobromite can be prepared in situ by reacting bromine water with sodium hypochlorite or potassium hypochlorite. By taking sodium hypochlorite as an example again, the reactions are as follows.

$$RCHO + Br_2 + 3OH^- = RCOO^- + 2Br^- + 2H_2O \quad (1)$$

$$RCHO + NaClO \xrightarrow{Br^-, OH^-} RCOOH + NaCl \quad (2)$$

In this embodiment, the added bromine oxidizes part of the raw material oligomannuronic acids and generates bromide ions; the bromide ions can in turn catalyze the sodium hypochlorite to continuously react with the unreacted raw material until the reaction is completed.

The oxidation step of the invention is conducted at pH of 6-10, preferably 6.5-9.6, more preferably 7.5-9.5. The oxidation step of the invention is conducted at a temperature of preferably 0-70° C., more preferably 10-45° C.

The thus-prepared oligomannuronic diacids can be purified. For example, alcohols such as ethanol or methanol can be used for precipitation. The precipitate is is then subject to redissolution and secondary alcohol precipitation. Oily precipitate is isolated with a separating funnel. The oily precipitate is dried to obtain the desired oligomannuronic diacids. If refining is needed to further remove residual monosaccharides, organic acid impurities, and inorganic salts in the product, it can be achieved by membrane dialysis or column chromatograph. These operations are known to those skilled in the art. The examples provided below illustrate some embodiments thereof.

Another aspect of the invention provides use of an oxidant that functions by bromine ions or hypobromite ions (BrO$^-$) in the oxidation of reducing oligosaccharides or polysaccharides, wherein the oxidant is selected from the group consisting of bromine water, liquid bromine, a mixture that produces hypobromite in situ, the combination of a metal bromide with hypochlorite, and the combination of bromine-sodium hypochlorite.

In an embodiment, the aldehyde group or hemiacetal at C1 position of the saccharide ring at the reducing end of the reducing oligosaccharide or polysaccharide is oxidized to a carboxyl group to produce the corresponding saccharic acid or saccharic diacids. In an embodiment, the reducing oligosaccharide or polysaccharide is selected from the group consisting of polymannuronic acid and polyguluronic acids, and preferably polymannuronic acid.

The advantages of the invention are further illustrated in the non-limiting is examples below. However, it would be appreciated that the specific materials and amounts thereof and the other experimental conditions utilized in the examples are not limitations to the invention. Unless indicated otherwise, the parts, ratios, percentages, etc. in the invention are by weight.

EXAMPLE

Example 1

Step 1): Preparation of M-Segment Oligosaccharides 1500 g M-segment intermediates were weighted and dissolved with distilled water to formulate a solution of 7500 ml volume. The solution was adjusted to pH 3.5 with concentrated hydrochloric acid, divided into several parts, placed into an autoclave to heat at 110° C. for 3.5 hours, cooled and removed, concentrated in a rotary evaporator, and dried in a vacuum oven at 60° C. to obtain 1515 g M-segment oligosaccharides.

The M-segment oligosaccharides were qualitatively analyzed by HPLC-MS. HPLC conditions: chromatographic column, Waters ACQUITY UPLC BEH125 SEC 1.7 μm, 4.6×300 mm; mobile phase: 50 mM NH$_4$Ac dissolved in 20% methanol-water, flow rate of 0.1 ml/min; sample concentration: 1 mg/ml; injection volume: 8 μl; column incubator temperature: 30° C.; detector: DAD detector, 210 nm. MS conditions: Agilent 6540 QTOF; ion source: ESI; fragmentation voltage: 120V; anion mode.

The M-segment oligosaccharide products obtained by acid degradation were all oligomannuronic acids, which were mainly disaccharides to tridecasaccharides. The MS analysis of disaccharides to tridecasaccharides is shown in the left half of Table 1 below.

Step 2): Preparation of Oligomannuronic Diacids 100 g of the above anhydrous M-segment oligosaccharides was placed into a 5 L glass beaker, dissolved with 1 L distilled water, added with 1 L of 1 M $Na_2HPO_4$, and is adjusted to pH 8.0 with concentrated hydrochloric acid. 3.3 L of commercially available 3% bromine water was slowly added with stirring at room temperature (20° C.) within 10 minutes. The reaction mixture was continually stirred for 2 hours before completion.

The solution after reaction was poured into a plastic bucket containing 4 L of 95% ethanol and stood for 1 hour after gently stirring. After standing and layering, the supernatant was removed, and the lower layer was dehydrated by adding a suitable amount of 95% ethanol. The tawny oily substance in the lower layer was collected and dried under reduced pressure in a vacuum oven (60° C.) for 12 hours to obtain the dried oxidation products, which were 125 g oligomannuronic diacids. A small amount of the dry oligomannuronic diacids was took out and weighted accurately to be 5.0 g, which was dissolved by adding water to formulate a 10% solution. The solution was desalted by dialysis with a dialysis bag of molecular cut off of 1000 Da, and monosaccharide was also removed. It was concentrated and dried after desalting and weighted to be 3.8 g. By calculating from the raw materials for the oxidation reaction, 100 g M-segment oligosaccharides, the yield of the oligomannuronic diacids after desalting and drying was 95.0%.

The above products after desalting and drying were qualitatively analyzed by HPLC-MS. HPLC conditions: chromatographic column, Waters ACQUITY UPLC BEH125 SEC 1.7 μm, 4.6×300 mm; mobile phase: 50 mM $NH_4Ac$ dissolved in 20% methanol/water, flow rate of 0.1 ml/min; sample concentration: 1 mg/ml; injection volume: 8 μl; column incubator temperature: 30° C.; detector: DAD detector, 210 nm. MS conditions: Agilent 6540 QTOF; ion source: ESI; fragmentation voltage: 120V; anion mode. The completeness of the oxidation reaction was above 95%, and no additional side reactions occurred. The desalting operation removed most monosaccharides and a few disaccharides. The MS analysis of disaccharides to tridecasaccharides of the oxidation products, oligomannuronic diacids, is shown in the right half of Table 1 below.

TABLE 1

MS analysis of oligomannuronic acids and oxidation products thereof.

| Oligomannuronic acids | m/z | Signal assignment | Oligomannuronic diacids | m/z | Signal assignment |
|---|---|---|---|---|---|
| Disaccharide | 739.14 | $[2M - H]^-$ | Disaccharide | 771.14 | $[2M - H]^-$ |
|  | 369.07 | $[M - H]^-$ |  | 385.07 | $[M - H]^-$ |
| Trisaccharide | 545.10 | $[M - H]^-$ | Trisaccharide | 561.10 | $[M - H]^-$ |
|  |  |  |  | 280.05 | $[M - 2H]^{2-}$ |
| Tetrasaccharide | 721.13 | $[M - H]^-$ | Tetrasaccharide | 737.12 | $[M - H]^-$ |
|  | 360.06 | $[M - 2H]^{2-}$ |  | 368.06 | $[M - 2H]^{2-}$ |
| Pentasaccharide | 897.17 | $[M - H]^-$ | Pentasaccharide | 913.15 | $[M - H]^-$ |
|  | 448.08 | $[M - 2H]^{2-}$ |  | 456.07 | $[M - 2H]^{2-}$ |
| Hexasaccharide | 1073.20 | $[M - H]^-$ | Hexasaccharide | 1089.21 | $[M - H]^-$ |
|  | 536.09 | $[M - 2H]^{2-}$ |  | 544.10 | $[M - 2H]^{2-}$ |
| Heptasaccharide | 1249.23 | $[M - H]^-$ | Heptasaccharide | 1265.21 | $[M - H]^-$ |
|  | 624.11 | $[M - 2H]^{2-}$ |  | 632.10 | $[M - 2H]^{2-}$ |
| Octasaccharide | 712.13 | $[M - 2H]^{2-}$ | Octasaccharide | 1441.28 | $[M - H]^-$ |
|  |  |  |  | 720.14 | $[M - 2H]^{2-}$ |
| Nonasaccharide | 1601.97 | $[M - H]^-$ | Nonasaccharide | 1617.30 | $[M - H]^-$ |
|  | 800.14 | $[M - 2H]^{2-}$ |  | 808.15 | $[M - 2H]^{2-}$ |
|  |  |  |  | 538.43 | $[M - 3H]^{3-}$ |
| Decasaccharide | 888.16 | $[M - 2H]^{2-}$ | Decasaccharide | 896.17 | $[M - 2H]^{2-}$ |
|  |  |  |  | 597.11 | $[M - 3H]^{3-}$ |
| Undecasaccharide | 976.17 | $[M - 2H]^{2-}$ | Undecasaccharide | 984.19 | $[M - 2H]^{2-}$ |
|  | 650.45 | $[M - 3H]^{3-}$ |  | 655.79 | $[M - 3H]^{3-}$ |
| Dodecasaccharide | 1064.69 | $[M - 2H]^{2-}$ | Dodecasaccharide | 1072.20 | $[M - 2H]^{2-}$ |
|  | 709.13 | $[M - 3H]^{3-}$ |  | 714.47 | $[M - 3H]^{3-}$ |
|  |  |  |  | 535.60 | $[M - 4H]^{4-}$ |
| Tridecasaccharide | 1152.70 | $[M - 2H]^{2-}$ | Tridecasaccharide | 1160.72 | $[M - 2H]^{2-}$ |
|  | 768.14 | $[M - 3H]^{3-}$ |  | 773.15 | $[M - 3H]^{3-}$ |
|  |  |  |  | 579.61 | $[M - 4H]^{4-}$ |

Example 2

Figure 2:
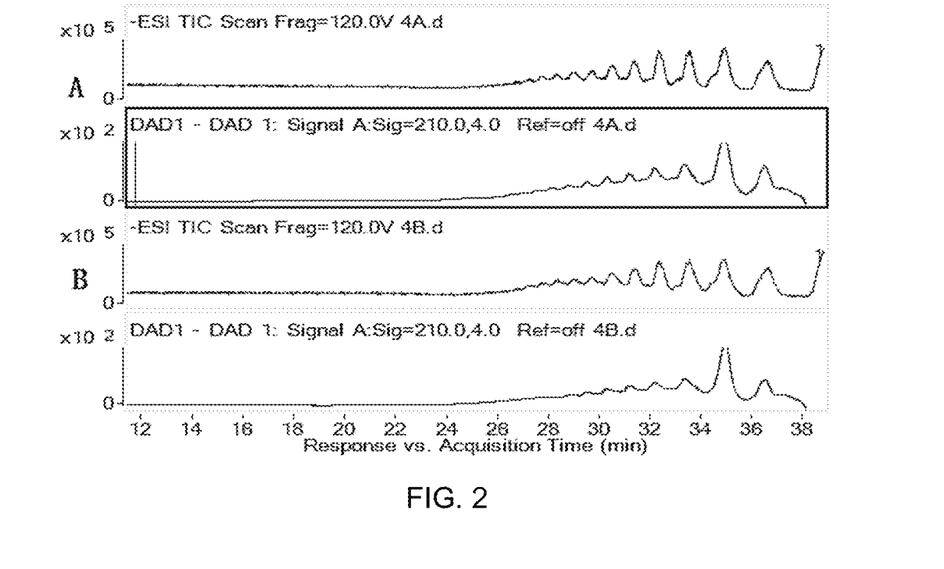
FIG. 2 shows SEC-HPLC graph of the resulting oligomannuronic diacids from the oxidation with bromine water.

100 g of the M-segment oligosaccharides prepared in Example 1 was placed into a 5 L glass beaker, dissolved with 1 L distilled water, added with 1 L of 1 M $Na_2HPO_4$, adjusted to pH 6.5 with concentrated hydrochloric acid, heated to 40° C. in water bath, and stirred. 1.7 L of commercially available 3% bromine water was slowly added within 10 minutes. After continually stirring for 3 hours, the reaction was terminated by adding 2 fold volume of 95% ethanol and the products were precipitated. The precipitate was dissolved with a suitable amount of water, and the alcohol precipitation operation was repeated once. At last, the precipitate was dried in a vacuum oven to obtain a 96 g brown brick solid, with a yield of about 96%. The composition of the solid substance was analyzed by HPLC-MS, with the same experimental conditions as Example 1. The SEC-HPLC analysis result is shown in FIG. 2A.

Example 3

100 g of the M-segment oligosaccharides prepared in Example 1 was placed into a 5L glass beaker, dissolved with 1 L distilled water, added with 1 L of 1 M $Na_2HPO_4$, adjusted to pH 9.5 with concentrated hydrochloric acid, cooled to 10° C. in water bath by adding a suitable amount of ice, and stirred. 4.7 L of commercially available 3% bromine water was slowly added within 10 minutes. After continually stirring for 1 hour, the reaction was terminated by adding 2 fold volume of 95% ethanol and the products were precipitated. The precipitate was dissolved with a suitable amount of water, and the alcohol precipitation operation was repeated once. At last, the precipitate was dried in a vacuum oven to obtain a 94 g brown brick solid, with a yield of about 94%. The composition of the solid substance was analyzed by HPLC-MS, with the same experimental conditions as Example 1. The SEC-HPLC analysis result is shown in FIG. 2B.

Example 4

Figure 3:
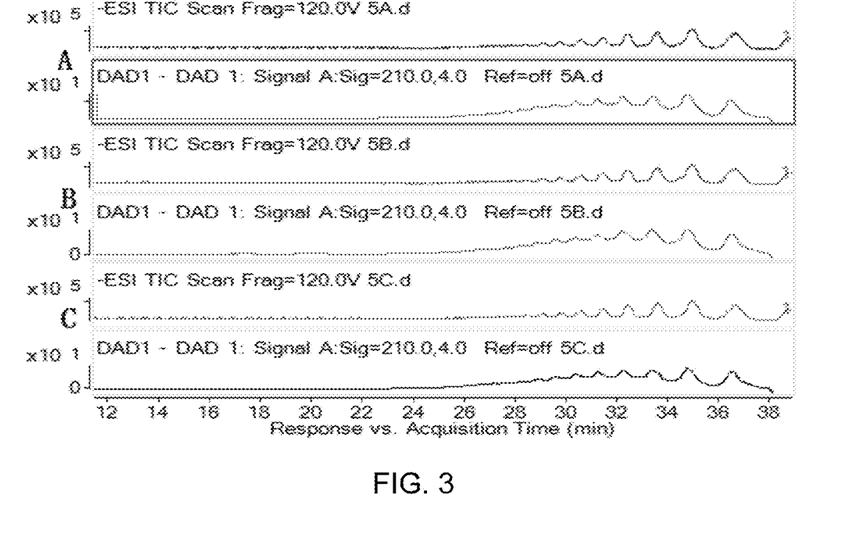
FIG. 3 shows SEC-HPLC graph of the resulting oligomannuronic diacids from the oxidation with liquid bromine.

100 g of the M-segment oligosaccharides prepared in Example 1 was dissolved in 500 ml of 1 M $Na_2HPO_4$ buffer, adjusted to pH 8.0 with hydrochloric acid, stirred in ice water bath to cool down, and slowly added with 100 g (about 35 ml) liquid bromine (commercially avaliable, content >99%). While the liquid bromine was added dropwise, a suitable amount of 6 M NaOH was supplemented. The pH of the reaction solution was tested with pH paper and controlled to be between 7 and 9. After the dropwise addition of the liquid bromine was completed, the ice water bath was removed. After stirring at room temperature (23° C.) for 1.5 hours, the reaction was terminated by addition of 2 fold volume of 95% ethanol, and the products were is precipitated. The precipitate was dissolved with a suitable amount of water, and the alcohol precipitation operation was repeated once. At last, the precipitate was dried in a vacuum oven to obtain a 97 g brown brick solid, with a yield of about 97%. The composition of the solid substance was analyzed by HPLC-MS, with the same experimental conditions as Example 1. The SEC-HPLC analysis result is shown in FIG. 3A.

Example 5

100 g of the M-segment oligosaccharides prepared in Example 1 was dissolved in 500 ml of 1 M $Na_2HPO_4$ buffer, adjusted to pH 6.5 with hydrochloric acid, stirred in ice water bath to cool down, and slowly added with 60 g (about 20 ml) liquid bromine (commercially avaliable, content >99%). While the liquid bromine was added dropwise, a suitable amount of 6 M NaOH was supplemented. The pH of the reaction solution was tested with pH paper and controlled to be between 7 and 9. After the dropwise addition of the liquid bromine was completed, the ice water bath was removed. After heating in water bath to 40° C. and stirring for 3 hours, the reaction was terminated by addition of 2 fold volume of 95% ethanol, and the products were precipitated. The precipitate was dissolved with a suitable amount of water, and the alcohol precipitation operation was repeated once. At last, the precipitate was dried in a vacuum oven to obtain a 94 g brown brick solid, with a yield of about 94%. The composition of the solid substance was analyzed by HPLC-MS, with the same experimental conditions as Example 1. The SEC-HPLC analysis result is shown in FIG. 3B.

Example 6

100 g of the M-segment oligosaccharides prepared in Example 1 was dissolved in 500 ml of 1 M $Na_2HPO_4$ buffer, adjusted to pH 9.5 with hydrochloric acid, stirred in ice water bath to cool down, and slowly added with 150 g (about 50 ml) liquid bromine (commercially available, content >99%). While the liquid bromine was added dropwise, a suitable amount of 6 M NaOH was supplemented. The pH of the reaction is solution was tested with pH paper and controlled to be between 7 and 9. After the dropwise addition of the liquid bromine was completed, the ice water bath was removed. A suitable amount of ice was added into the water bath such that the temperature reached 10° C. after ice melted, and ice was supplemented anytime necessary such that the temperature was controlled to be 10° C. After stirring for 1 hour, the reaction was terminated by addition of 2 fold volume of 95% ethanol, and the products were precipitated. The precipitate was dissolved with a suitable amount of water, and the alcohol precipitation operation was repeated once. At last, the precipitate was dried in a vacuum oven to obtain a 93 g brown brick solid, with a yield of about 93%. The composition of the solid substance was analyzed by HPLC-MS, with the same experimental conditions as Example 1. The SEC-HPLC analysis result is shown in FIG. 3C.

Example 7

100 g of the M-segment oligosaccharides prepared in Example 1 was dissolved in 500 ml of 1 M $Na_2HPO_4$ buffer and adjusted to pH 8.0 with hydrochloric acid to obtain an M-segment oligosaccharide solution. A 100 ml of 6M NaOH solution was formulated and cooled in ice water bath. Liquid bromine was also pre-cooled in ice water bath. Upon the reaction, the NaOH solution was reacted with the liquid bromine to produce sodium hypobromite, and then the sodium hypobromite was reacted with the M-segment oligosaccharides.

Since sodium hypobromite was not stable, it needed to be prepared immediately before use. Thus, an on-line continuous reactor device was applied: the reactor device included a mixing reactor A equipped with a cooling element and a mixing reactor B, with volumes of 50 ml and 100 ml, respectively, and prefilled with distilled water; NaOH solution and liquid bromine were separately, manually, and continuously pumped in via plastic syringes at constant rates of 5 ml/min and 1 ml/min, respectively, while cooling liquid at −10° C. was passed through the condensation tube of the reactor A; after the NaOH solution and liquid bromine were reacted in the mixing reactor A for a period of time, the resulting NaBrO exited the reactor A and entered into the is reactor B to react with the M-segment oligosaccharide solution (flow rate of 10 ml/min) pumped in the reactor B at room temperature. The product oligomannuronic diacids flowed out the mixing reactor B at a rate of 16 ml/min. The effluent was collected in a beaker containing 800 ml of 95% ethanol.

Figure 4:
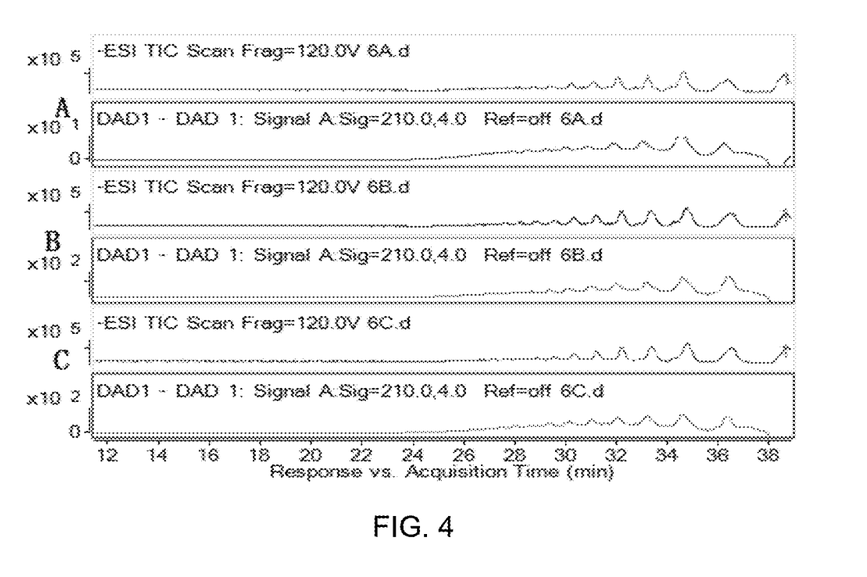
FIG. 4 shows SEC-HPLC graph of the resulting oligomannuronic diacids from the oxidation with NaBrO.

After the reaction was completed, the tawny oily precipitate in the lower layer in the beaker was collected, subject to alcohol precipitation operation again after it was dissolved with a suitable amount of water, and dried at reduced pressure in a vacuum oven (60° C., 12 hours) to obtain a 90 g brown solid with a yield of about 90%. A small amount of the dry product was taken for HPLC-MS analysis. The SEC-HPLC analysis result is shown in FIG. 4A.

Example 8

100 g of the M-segment oligosaccharides prepared in Example 1 was dissolved in 500 ml of 1 M $Na_2HPO_4$ buffer and adjusted to pH 6.5 with hydrochloric acid. A 100 ml of 6M NaOH solution was formulated and cooled in ice water bath. Liquid bromine was also pre-cooled in ice water bath. To carry out the reaction, the NaOH solution was reacted with the liquid bromine to produce sodium hypobromite, which was then reacted with the M-segment oligosaccharides.

The reactor device was the same as that in Example 7. The flow rates at which the NaOH solution and liquid bromine entered into the reactor A were 3 ml/min and 0.6 ml/min, respectively; the flow rate of the M-segment oligosaccharide solution in the reactor B was 10 ml/min. The reaction was controlled by water bath to have a temperature of 40° C. The product oligomannuronic diacids flowed out the mixing reactor B at a rate of 14 ml/min. The effluent was collected in a beaker containing 800 ml of 95% ethanol. After the reaction was completed, the tawny oily precipitate in the lower layer in the beaker was collected, and subject to alcohol precipitation operation again after it was dissolved with a suitable amount of water. At last, the precipitate was dried at reduced pressure in a vacuum oven (60° C., 12 hours) to obtain a 93 g brown solid with a yield of about 93%. A small amount of the dry product was taken for HPLC-MS analysis. The SEC-HPLC analysis result is shown in FIG. 4B.

Example 9

100 g of the M-segment oligosaccharides prepared in Example 1 was dissolved in 500 ml of 1 M $Na_2HPO_4$ buffer and adjusted to pH 9.5 with hydrochloric acid to obtain an M-segment oligosaccharide solution. A 100 ml of 6M NaOH solution was formulated and cooled in ice water bath. Liquid bromine was also pre-cooled in ice water bath. To carry out reaction, the NaOH solution was preliminarily reacted with the liquid bromine to produce sodium hypobromite, which was then reacted with the M-segment oligosaccharides.

The reactor device was the same as that in Example 7. The flow rates at which the NaOH solution and liquid bromine entered into the reactor A were 7.5 ml/min and 1.5 ml/min, respectively; the flow rate of the M-segment oligosaccharide solution in the reactor B was 10 ml/min. The reaction was controlled to have a temperature of 10° C. The product oligomannuronic diacids flowed out the mixing reactor B at a rate of 19 ml/min. The effluent was collected in a beaker containing 800 ml of 95% ethanol. After the reaction was completed, the tawny oily precipitate in the lower layer in the beaker was collected, and subject to alcohol precipitation operation again after it was dissolved with a suitable amount of water. At last, the precipitate was dried at reduced pressure in a vacuum oven (60° C., 12 hours) to obtain a 94 g brown solid with a yield of about 94%. A small amount of the dry product was taken for HPLC-MS analysis. The SEC-HPLC analysis result is shown in FIG. 4C.

Example 10

100 g of the M-segment oligosaccharides prepared in Example 1 was dissolved in 500 ml of 1 M $Na_2HPO_4$ buffer, adjusted to pH 7.5 with hydrochloric acid, added with 20 g sodium bromide with stirring till dissolved, and added dropwise with 50 ml of sodium hypochlorite (commercially available, as 13% solution) at room temperature (18° C.). The reaction solution faded, and then reddish brown color gradually appeared. The color faded after the reaction proceeded for a period of time. After the reaction proceeded for 3 hours, the color became orange-yellow.

Figure 5:
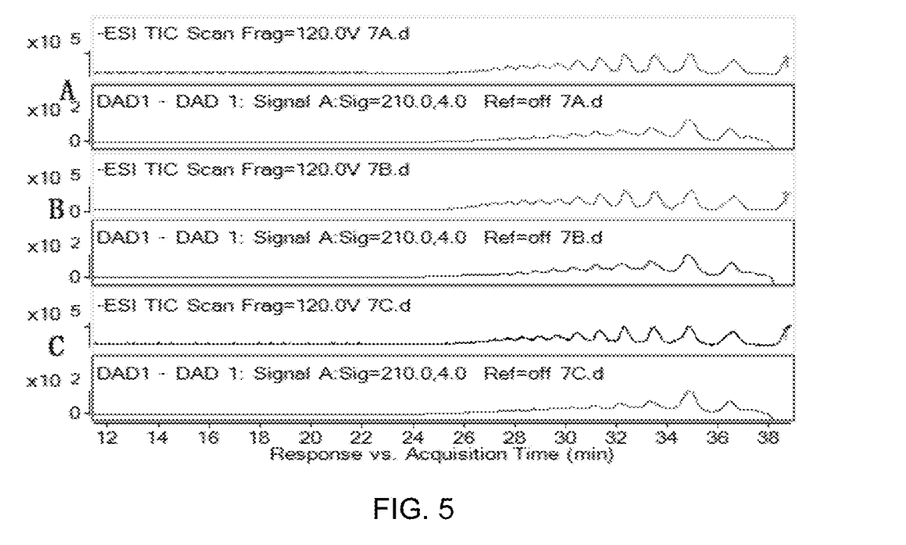
FIG. 5 shows SEC-HPLC graph of the resulting oligomannuronic diacids from the oxidation of sodium hypochlorite catalyzed by sodium bromide.

The reaction solution was poured in a beaker containing 600 ml of 95% ethanol, mixed evenly, and stood still for layering. The lower layer liquid was dissolved with a suitable amount of water, re-precipitated by using 2 fold volume of 95% ethanol, and dried at reduced pressure in a vacuum oven at 60° C. for 12 hours. A 97 g brown solid was obtained after drying with a yield of about 97%. A small amount was taken for HPLC-MS analysis. The SEC-HPLC analysis result is shown in FIG. 5A.

Example 11

100 g of the M-segment oligosaccharides prepared in Example 1 was dissolved in 500 ml of 1 M $Na_2HPO_4$ buffer, adjusted to pH 6.5 with hydrochloric acid, added with 20 g sodium bromide with stirring till dissolved, and added dropwise with 25 ml of sodium hypochlorite (commercially available, as 13% solution) at 40° C. The reaction solution faded, and then reddish brown color gradually appeared. The color faded after the reaction proceeded for a period of time. After the reaction proceeded for 3 hours, the color became orange-yellow. The reaction solution was poured in a beaker containing 600 ml of 95% ethanol, mixed evenly, and stood still for layering. The lower layer liquid was dissolved with a suitable amount of water, re-precipitated by using 2 fold volume of 95% ethanol, and dried at reduced pressure in a vacuum oven at 60° C. for 12 hours. A 90 g brown solid was obtained after drying with a yield of about 90%. A small amount was taken for HPLC-MS analysis. The SEC-HPLC analysis result is shown in FIG. 5B.

Example 12

100 g of the M-segment oligosaccharides prepared in Example 1 was dissolved in 500 ml of 1 M $Na_2HPO_4$ buffer, adjusted to pH 9.5 with hydrochloric acid, added with 20 g sodium bromide with stirring till dissolved, and added dropwise with 75 ml of sodium hypochlorite (commercially available 13% solution) at 40° C. The reaction solution faded, and then reddish brown color gradually appeared. The color faded after the reaction proceeded for a period of time. After the reaction proceeded for 1 hour, the color became orange-yellow. The reaction solution was poured in a beaker containing 600 ml of 95% ethanol, mixed evenly, and stood still for layering. The ower layer liquid was dissolved with a suitable amount of water, re-precipitated by using 2 fold volume of 95% ethanol, and dried at reduced pressure in a vacuum oven at 60° C. for 12 hours. A 96 g brown solid was obtained after drying with a yield of about 96%. A small amount was taken for HPLC-MS analysis. The SEC-HPLC analysis result is shown in FIG. 5C.

Example 13

Figure 6:
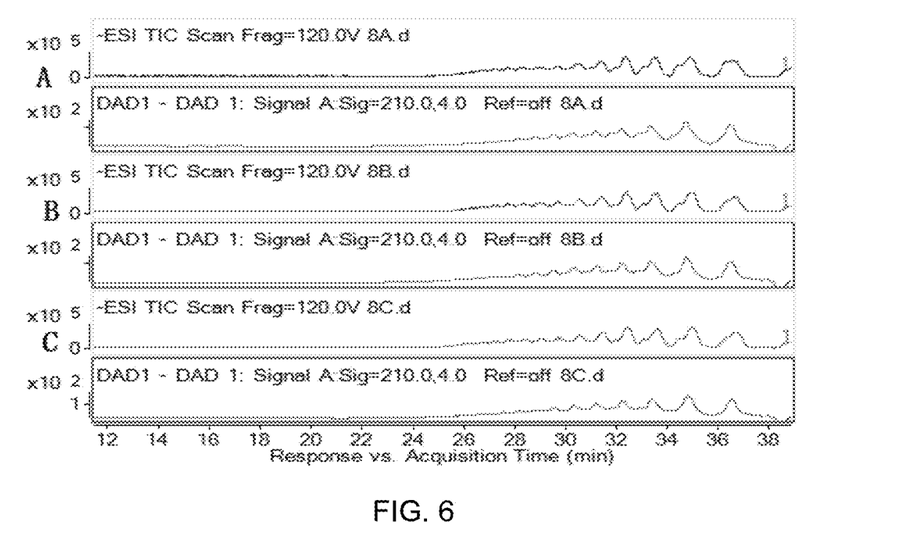
FIG. 6 shows SEC-HPLC graph of the resulting oligomannuronic diacids from the oxidation with bromine-sodium hypochlorite.

100 g of the M-segment oligosaccharides prepared in Example 1 was dissolved in 500 ml of 1 M $Na_2HPO_4$ buffer, adjusted to pH 8.5 with hydrochloric acid, added dropwise with 10 ml liquid bromine with stirring at room temperature. After this, the reaction was further added with 35 ml sodium hypochlorite (commercially available, as 13% solution). The reaction proceeded for 1 hour. After the reaction was completed, the reaction was terminated by adding 2 fold volume of 95% ethanol and stood still for layering. The tawny oily precipitate in the lower layer was subject to alcohol precipitation operation again after it was dissolved with a suitable amount of water. At last, the precipitate was dried at reduced pressure in a vacuum oven to obtain 91 g solid, with a yield of about 91%. A small amount of the sample was taken for HPLC-MS analysis. The SEC-HPLC analysis result is shown in FIG. 6A.

Example 14

100 g of the M-segment oligosaccharides prepared in Example 1 was dissolved in 500 ml of 1 M $Na_2HPO_4$ buffer, adjusted to pH 6.5 with hydrochloric acid, heated to 40° C. in water bath, added dropwise with 8 ml liquid bromine with stirring. After that, the reaction was further added with 20 ml sodium hypochlorite (commercially available, 13% concentration). The reaction proceeded for 3 hours. The reaction process was shown as Formula (V) in Example 13. The added bromine oxidized part of the raw material oligomannuronic acids and generated bromide ions; the bromide ions in turn catalyzed the sodium hypochlorite to continuously react with the unreacted raw material until the reaction was completed. After the reaction was completed, the reaction was terminated by adding 2 fold volume of 95% ethanol and stood still for layering. The tawny oily precipitate in the lower layer was subject to alcohol precipitation operation again after it was dissolved with a suitable amount of water. At last, the precipitate was dried at reduced pressure in a vacuum oven to obtain 96 g with a yield of about 96%. A small amount of the sample was taken for HPLC-MS analysis. The SEC-HPLC analysis result is shown in FIG. 6B.

Example 15

100 g of the M-segment oligosaccharides prepared in Example 1 was dissolved in 500 ml of 1 M $Na_2HPO_4$ buffer, adjusted to pH 9.5 with hydrochloric acid, while the temperature was controlled to be 10° C. by adding ice in water bath, added dropwise with 15 ml liquid bromine with stirring. After that, the reaction was further added with 50 ml sodium hypochlorite (commercially available, 13% concentration). The reaction proceeded for 0.5 hour. The reaction process was shown as Formula (V) in Example 13. The added bromine oxidized part of the raw material oligomannuronic acids and generated bromide ions; the bromide ions in turn catalyzed the sodium hypochlorite to continuously react with the unreacted raw material until the reaction was completed. After the reaction was completed, the reaction was terminated by adding 2 fold volume of 95% ethanol and stood still for layering. The tawny oily precipitate in the lower layer was subject to alcohol precipitation operation again after it was dissolved with a suitable amount of water. At last, the precipitate was dried at reduced pressure in a vacuum oven to obtain 94 g solid, with a yield of about 94%. A small amount of the sample was taken for HPLC-MS analysis. The SEC-HPLC analysis result is shown in FIG. 6C.

Example 16

Figure 7A:
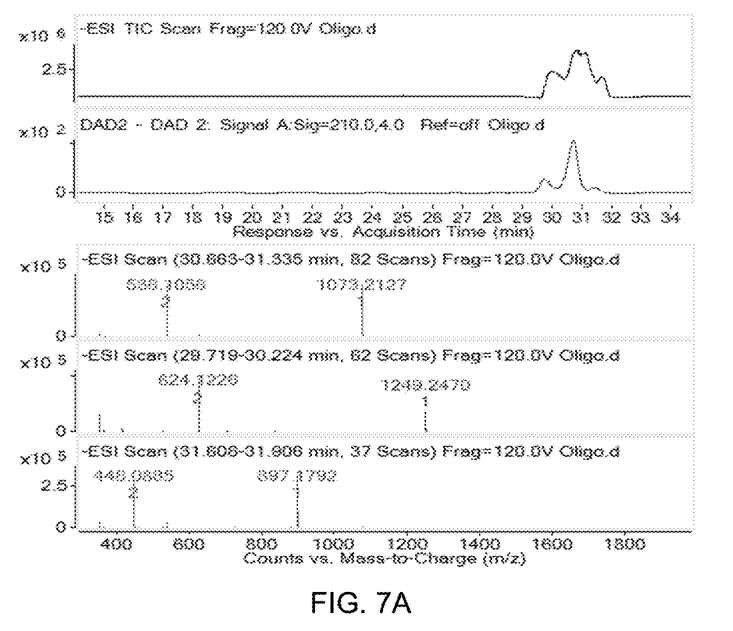
FIG. 7A and FIG. 7B respectively shows LC-MS graphs of the hexaose components of mannuronic acid before and after oxidation (with bromine water-sodium hypochloride).

10 g of the M-segment oligosaccharides prepared in Example 1 was dissolved in water to formulate 0.1 g/ml, isolated using Bio-Gel P6 gel chromatographic column, eluted with 0.02 M NaCl, detected at UV 210 nm, and collected by automatic collector. The same components were combined, desalted by using Bio-Gel P10 gel chromatographic column, and dried to obtain the 10 oligosaccharide components. One oligosaccharide component of them was marked as HexaM. HexaM was analyzed by HPLC-MS to show that it contained mostly oligomannuronic acid hexasaccharides, while a small amount of pentasaccharides and heptasaccharides existed. See FIG. 7A for details.

Figure 7B:
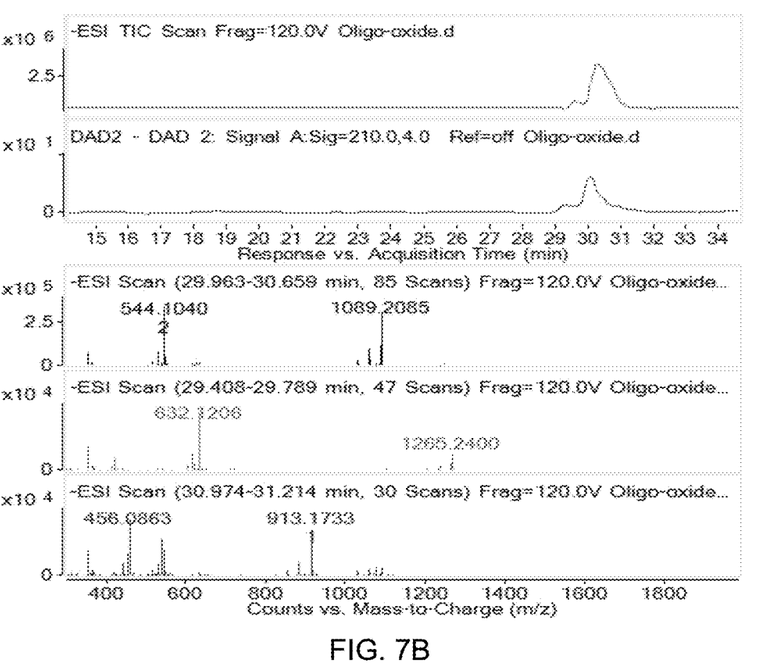

0.5 g of the above HexaM was weighted, dissolved in 5 ml water, transferred to a 50 ml rounded bottom flask, added with 5 ml of 1M $Na_2HPO_4$, adjusted to pH 7.9 with 6 M HC1, kept at 20° C. room temperature, stirred on a magnetic stirrer, added dropwise with 1.0 ml of commercially available 3% concentration bromine water and stirred for 30 minutes, added dropwise with 0.5 ml sodium hypochlorite (commercial 13% concentration) and stirred for 1 hour, added with 10 ml of 95% ethanol to terminate the reaction and produce precipitate. The precipitate was re-dissolved with 10 ml water and precipitated again by adding ethanol. Supernatant was removed with pipette, and the precipitate was collected and dried in a vacuum oven at 60° C. to obtain a 0.48 g solid. A suitable amount of the solid was taken for HPLC-MS analysis by the same analysis method as Example 1. The analysis result shows that the major components in the reaction raw material, mannuronic acid hexasaccharides, were oxidized to mannuronic diacid hexasaccharides, with reaction completeness of >98%. The LC-MS analysis result is shown in FIG. 7B.

The invention claimed is:

1. A method of preparing oligomannuronic diacids, comprising an oxidation reaction step of contacting oligomannuronic acids with a bromine-containing oxidant, wherein the bromine-containing oxidant is selected from the group consisting of bromine water, liquid bromine, hypobromous acid, hypobromite, a combination of a bromide ion source with hypochlorite, and a combination of bromine with hypochlorite; wherein the temperature of the oxidation reaction is 10-40° C.; and wherein the pH of the oxidation reaction is controlled to be between 6.5 and 9.5.

2. The method of claim 1, wherein the molar amount of the bromine-containing oxidant calculated based on hypobromous acid or hypochlorite is 1.0-2.0 folds of the reaction raw material oligomannuronic acid.

3. The method of claim 1, wherein the hypobromous acid or hypobromite is obtained by in situ production.

4. The method of claim 3, wherein the in situ production is achieved by the reaction of bromine with an aqueous alkaline solution.

5. The method of claim 4, wherein the aqueous alkaline solution is an aqueous solution of an alkali metal hydroxide or an alkali metal phosphate or an alkali metal carbonate.

6. The method of claim 1, wherein the hypobromite or hypochlorite is an alkali metal salt.

7. The method of claim 1, wherein the oligomannuronic acids contain 2-20 mannuronic acid units.

8. The method of claim 7, wherein the oligomannuronic acids are obtained by degradation of polymannuronic acid with a higher polymerization degree.

9. The method of claim 8, wherein the degradation is degradation under an acidic condition.

10. The method of claim 9, wherein the polymannuronic acid is formulated into a concentrated solution with a concentration of more than 15% (w/v) and a pH adjusted to below 5.0 to allow the degradation of the polymannuronic acid.

11. The method of claim 8, wherein the polymannuronic acid has a polymerization degree of more than 20.

12. The method of claim 1, wherein the molar amount of the bromine-containing oxidant calculated based on hypobromous acid or hypochlorite is 1.0-2.0 folds of the reaction raw material oligomannuronic acid.

13. The method of claim 9, wherein the polymannuronic acid has a polymerization degree of more than 20.

14. The method of claim 10, wherein the polymannuronic acid has a polymerization degree of more than 20.

15. The method of claim 5, wherein the aqueous alkaline solution is an aqueous solution of sodium hydroxide or sodium phosphate or sodium carbonate.

16. The method of claim 6, wherein the alkali metal salt is a sodium salt or a potassium salt.

17. The method of claim 7, wherein the oligomannuronic acids contain mannuronic acid units selected from a group consisting of 2-15, 2-13, 3-12, 4-10, and 4-8 mannuronic acid units.

* * * * *